United States Patent [19]
Anderson et al.

[11] Patent Number: 6,044,694
[45] Date of Patent: *Apr. 4, 2000

[54] RESONATOR SENSORS EMPLOYING PIEZOELECTRIC BENDERS FOR FLUID PROPERTY SENSING

[75] Inventors: Philip D. Anderson, Wood Dale; Michael J. Rybicki, Downers Grove, both of Ill.

[73] Assignee: Videojet Systems International, Inc., Wood Dale, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/704,116

[22] Filed: Aug. 28, 1996

[51] Int. Cl.⁷ .................................................. G01N 11/16
[52] U.S. Cl. ..................... 73/54.41; 73/32 A; 73/54.27; 73/54.25
[58] Field of Search ................... 73/32 A, 54.24, 73/54.25, 54.26, 54.27, 54.41, 290 V

[56] References Cited

U.S. PATENT DOCUMENTS

| | | | |
|---|---|---|---|
| 2,707,391 | 5/1955 | McSkimin | 73/54.24 X |
| 2,973,639 | 3/1961 | Banks | 73/32 A |
| 3,220,258 | 11/1965 | Rod | 73/290 |
| 3,349,604 | 10/1967 | Banks . | |
| 3,903,732 | 9/1975 | Rork et al. | 73/32 A X |
| 4,484,862 | 11/1984 | Jensen . | |
| 4,644,789 | 2/1987 | Snyder | 73/290 V |
| 4,734,609 | 3/1988 | Jasmine | 73/703 X |
| 4,783,987 | 11/1988 | Hager et al. | 73/32 A |
| 4,922,745 | 5/1990 | Rudkin et al. | 73/32 A |
| 5,235,844 | 8/1993 | Bonne et al. | 73/24.01 |
| 5,571,952 | 11/1996 | Kauzlarich | 73/54.26 X |

FOREIGN PATENT DOCUMENTS

| | | | |
|---|---|---|---|
| 2436372 | 4/1980 | France . | |
| 3240 | 1/1988 | Japan | 73/54.41 |
| 683375 | 2/1994 | Switzerland . | |
| 1581291 | 12/1980 | United Kingdom . | |
| 2114745 | 8/1983 | United Kingdom . | |
| 2152665 | 8/1985 | United Kingdom . | |
| 2187286 | 9/1987 | United Kingdom | 73/32 A |
| 2200450 | 8/1988 | United Kingdom | 73/32 A |
| 95/13192 | 5/1995 | WIPO . | |
| 95/29388 | 11/1995 | WIPO . | |

OTHER PUBLICATIONS

Apparatus for sensing the level of particulate matter or liquid relative to a preselected level in a container Xerox Disclosure Journal vol. 19, No. 5, pp. 375–377, Author A. Cherian, Date Sep. 1994.

*Primary Examiner*—Daniel S. Larkin
*Attorney, Agent, or Firm*—Piper Marbury Rudnick & Wolfe

[57] ABSTRACT

Resonator sensors namely piezoelectric benders are used for sensing fluid viscosity and density. The benders are inserted into a liquid to be monitored. An input voltage is applied to the bender causing it to vibrate in the liquid at a resonant frequency. Output voltage amplitude or frequency are monitored to determine changes in viscosity and density, respectively. The device may be used as a liquid level sensor and to control alteration of the viscosity of the fluid as, for example, by connection with a supply of ink or solvent in an ink jet printing device.

19 Claims, 2 Drawing Sheets

RESONATOR SENSORS EMPLOYING PIEZOELECTRIC BENDERS FOR FLUID PROPERTY SENSING

BACKGROUND OF THE INVENTION

This invention relates to the field of fluid property sensing by which parameters such as fluid level, viscosity and density may be determined for a gas or liquid. The prior art for such devices is extensive, including devices dedicated to liquid level sensing, viscosity determination or density measurement. The present invention relates to the class of sensing devices generally known as resonating sensors. The advantages of resonating sensors have been well documented and several commercial devices exist. These include the vibrating wire viscometer, such as disclosed by James M. Goodwin in *Journal Of Physics*, Volume 6, 1973; the Dynatrol Viscometer manufactured by Automation Products, Inc.; tuning fork type viscometers, for example, of the type disclosed by M. R. Fisch, et al., *J. Acoustic Soc. Am.*, Volume 60, No. 3, September 1976, p. 623, and tuning fork type liquid level detectors, such as those manufactured by Endress & Hauser and Automation Products, Inc.

These prior art devices have several disadvantages. They require separate transducers in addition to a vibrating structure. They are assemblies of several components requiring exotic materials and/or intricate machining thereby increasing costs. Further, such devices are susceptible to corrosive materials, are larger than may be desired for some applications and have limited sensitivity ranges. Perhaps most significant, is the fact that these devices offer only one function, for example, either viscometry or level detection, but not both.

It is desirable in fluid handling systems to monitor the viscosity of the fluid to ascertain changes in its viscosity which may indicate the need for corrective action. It is also necessary to monitor the level of the fluid, which in the case of liquids, may indicate the need for replenishment. Although there are many applications which have these requirements, one environment for which the present invention in suited, is ink jet printing. In typical commercial ink jet printing systems, an electrically-conductive, oftentimes corrosive, marking fluid or ink is utilized for printing information on products. These may include date codes, bar codes, lot information and the like. Ink jet printers are well known devices and will not be discussed in detail in this disclosure. In order to keep such devices running properly over extended periods of time, the properties of the marking fluid must be monitored and modified when deviations from standard parameters are detected. Thus, the viscosity and/or density of the marking fluid must be monitored as well as the level of the fluid in the various reservoirs in which the marking fluid are kept.

In such systems, it is important to provide measurements of the fluid properties and to do so in an efficient, compact and economical way. Many of the prior art devices mentioned above can perform the desired functions in combination, but cannot do so as efficiently as would be desired.

It is accordingly an object of the present invention to provide for fluid property sensing using apparatus and methods which overcome these shortcomings. According to the present invention, a piezoelectric bender is adapted to this purpose. The term piezoelectric bender is meant to describe a class of devices which are commercially available, such as piezoelectric ceramic wafers which function as transducers between mechanical and electrical energy. One source of such devices is Morgan Matroc, Inc. of Bedford, Ohio. Such devices are often used as audio tone generators and as strain gauges for measuring tensile or compressive force, etc. The present invention adapts these devices to a new purpose not previously known in this art.

Piezoelectric benders, so-called because they are a composite structure which bends when a voltage is applied, and, conversely generate a voltage when strained. One type of bender manufactured by Morgan Matroc is known in the trade as a Bimorph. The Bimorph is a composite structure of two transverse-expander piezoelectric plates bonded together. This structure enhances the bending characteristics of the device and simplifies the electronics required to operate it.

According to the present invention, piezoelectric benders are employed for the dual purpose of detecting liquid level in a fluid system and for monitoring the viscosity and/or density of the fluid. The preferred embodiment accomplishes this by driving the piezoelectric bender at a voltage and frequency which cause it to resonate. By monitoring the output voltage from the bender, it is possible to monitor changes in the viscosity of a liquid or gas. Should the viscosity of such a liquid approach zero, this signifies that the device is no longer immersed in liquid, thereby performing level sensing as well. By measuring the natural resonant frequency instead of output voltage, the density of a liquid can be monitored.

In general, the invention relates to resonator sensors which may be implemented as fluid property sensors by measuring the effects of viscous damping and mass loading on the vibrating structure of the sensor and converting these measurements into the fluid property values of interest via predetermined relationships. These effects can be measured by monitoring an output magnitude and/or frequency. Other suitable techniques include measuring quality factor (Q), logarithmic decrement of free oscillation, decay time constant of free oscillation, electrical impedance characteristics (motional impedance and resistance), drive amplitude required to maintain constant output amplitude, and phase difference between input and output signals.

It is accordingly an object of the present invention to provide a new class of fluid sensing devices which are small, simple in construction, low in cost and which can accurately monitor properties of fluids including liquid level, viscosity and density. It is another object of this invention to provide such a class of devices for use in ink jet printing systems where the properties of liquid inks used in printing must be carefully monitored and altered when variations from desired specifications are detected. These and other objects of the invention will be apparent from the remaining portion of this specification.

DETAILED DESCRIPTION

Figure 1:
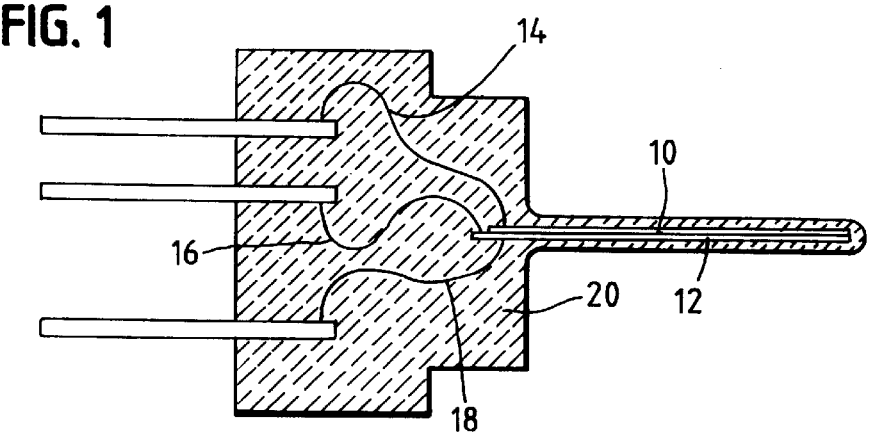
FIG. 1 illustrates a piezoelectric bender according to a preferred embodiment of the invention.

Referring to FIG. 1 there is shown in cross-section the basic structure of a piezoelectric bender suitable for use according to the present invention. Such devices are commercially available from a number of sources including Morgan Matroc, Inc. of Bedford, Ohio. Piezoelectric benders are piezoelectric ceramic devices made from lead metaniobate and lead zirconate titanate compositions. Such devices are available in a number of different configurations, including thin piezoelectric disks and double-plate ceramic elements.

The device shown in FIG. 1 is a cantilevered piezoelectric bender. Unlike standard piezoelectric crystals that only expand or contract, the composite structure of the device shown in FIG. 1 causes it to bend when a voltage is applied. Conversely, when the element is strained or flexed from its initial position, it generates a voltage. The bender illustrated is sold under the trade name Bimorph. Two transverse-expander piezoelectric plates are bonded together. They are identified in the drawing as elements 10 and 12. Elements 10 and 12 are electrically isolated to simplify the electronics required to obtain the result described herein. Standard wire tacking techniques are used to attach the leads 14, 16 and 18 required for external connection to control circuitry.

The plates 10 and 12 are encapsulated in a potting material 20. In the embodiment illustrated, the potting material forms a base or support element which can be used for mounting the sensor to a vessel in which the fluid to be monitored is contained. In the illustrated embodiment, a Bimorph device, the potting materials further serves to clamp one end of the bender to provide a cantilever structure. This structure is not required, but is a preferred embodiment due to its simplicity.

The FIG. 1 embodiment is preferred because it enhances the vibrating structure of the bender and because it is a suitable geometry to interface with fluids. The potting material also provides electrical insulation and protects the plates from corrosion. The potting material may preferably be formed of a quartz glass composition although other materials, including epoxies, plastics or composites may also be suitable.

Figure 2:
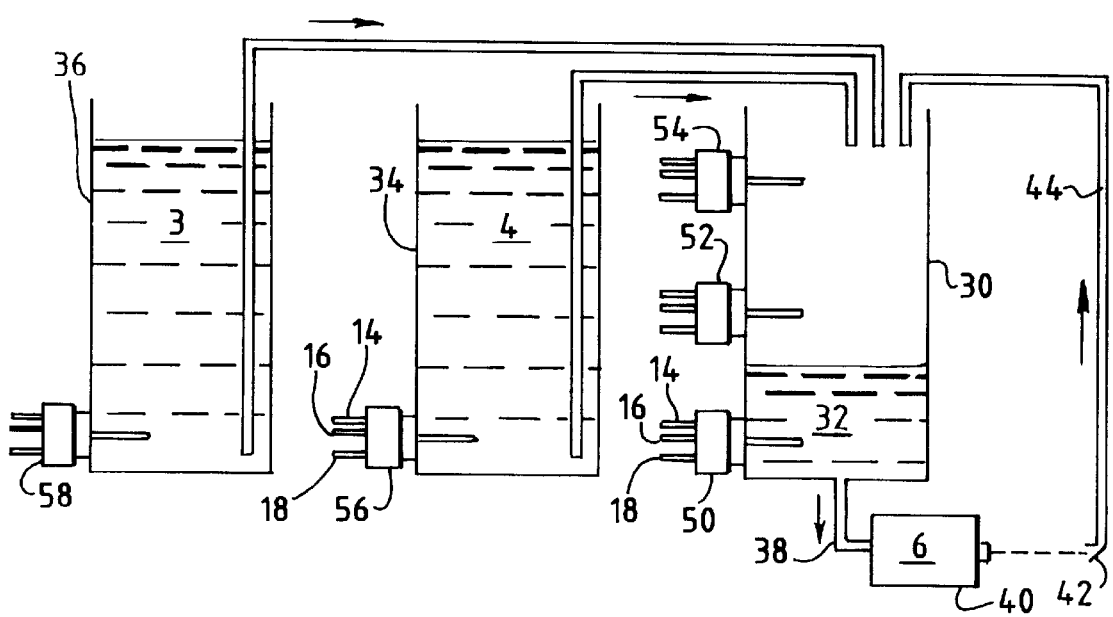
FIG. 2 illustrates the use of such piezoelectric benders in a typical ink jet printing system for use in monitoring the level and viscosity of ink.

Referring to FIG. 2, there is illustrated a fluid handling system in which the present invention may be employed. For purposes of exemplifying the invention only, the illustration in FIG. 2 relates to a fluid handling system of a continuous ink jet printer. Such a device includes a mixing vessel 30 containing a supply of marking fluid or ink 32. A vessel 34 contains a supply of fresh ink which is used periodically to refill the mixing vessel as ink is consumed during the printing processes. A third vessel 36 contains a supply of solvent used to maintain the composition of the ink in mixing vessel 30 within desired parameters. The solvent is added periodically to make up for evaporative losses as the ink in the mixing vessel 30 is recycled from a printing head 40. The ink from the mixing vessel 30 is conducted by conduit 38 to a remotely located printhead 40. Selected drops are electrically charged and then deflected onto a surface being marked. Uncharged drops are returned to the mixing vessel 30 by means of a collector 42 and a return conduit 44. Such an arrangement is typical for continuous-type ink jet printers and forms no part of the present invention. For more information concerning such systems, the reader is referred to U.S. Pat. Nos. 5,424,766 and 4,860,027 hereby incorporated by reference.

At the mixing vessel 30 it is desired to monitor the liquid level therein as well as the viscosity of the ink. This determines when it is necessary to provide additional fresh ink and/or solvent to prevent the ink from becoming too viscous due to evaporative losses.

According to the present invention, this may be accomplished by using piezoelectric benders of the type illustrated in FIG. 1 operated in a manner described hereafter. More specifically, the mixing vessel is preferably outfitted with three benders 50, 52 and 54. Bender 50 provides a dual function, namely, it determines both fluid level and viscosity. Benders 52 and 54, although capable of determining viscosity, are principally used to determine the level of the fluid in the mixing vessel 30. Additional benders in 56 and 58 may be provided in the fresh ink and solvent vessels 34 and 36 respectively for the same purpose, namely fluid level detection and, if desired, viscosity measurement.

As illustrated in FIG. 2, the encapsulated benders are mounted to the side of the vessels forming probes protruding into the vessels through openings provided therefor. The potting material 20 to which the one end of the plates is secured, serves as a surface for mounting the device to the vessel wall and to seal the vessel to prevent leakage. Thus, the piezoelectric plates 10 and 12, clamped at one end by the potting material 20 protrude into the mixing vessel to interact with any fluids contained therein. The electrical leads 14, 16 and 18 extending from the benders 50 through 58, are connected to the control circuitry described hereafter for measuring the viscosity and liquid level in the vessels.

Figure 3:
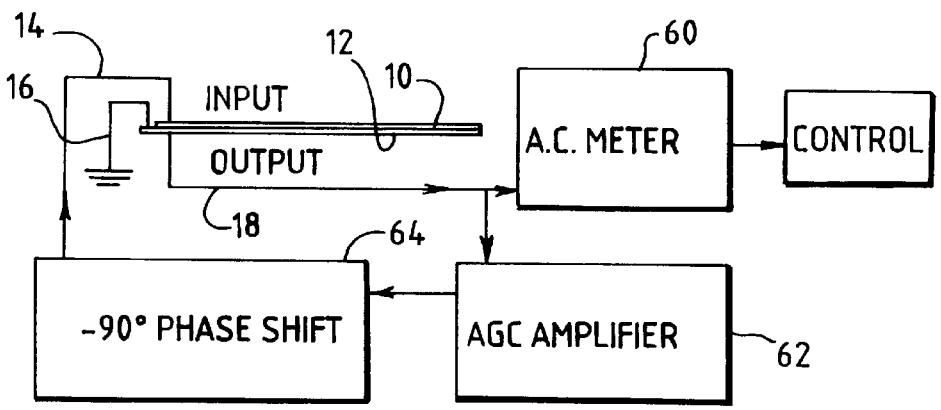
FIG. 3 illustrates, in block diagram form, the manner in which the piezoelectric bender is operated to obtain useful information therefrom.

With reference to FIGS. 1 and 3, the manner in which the benders are employed to sense viscosity and fluid level will be explained. As indicated previously, when the plates 10 has a voltage applied thereto, the plates 10 and 12 are caused to bend. Applying an AC voltage causes vibration of the benders. According to the present invention, viscosity is measured by measuring the effects of viscous damping on the vibration of the benders. The preferred embodiment, illustrated in FIG. 3, applies a voltage having an amplitude and frequency to optimize resonant vibration, of the bender. That is, the vibrating portion of the bender is driven at its fundamental resonant frequency by applying to it a voltage signal of proper amplitude and frequency. The frequency of the voltage is dependent on the environment in which the sensor operates. There are, however, many standard methods for determining the correct frequency.

Referring more specifically to FIG. 3, there is illustrated an embodiment, which is presently preferred, for driving the bender at its natural resonance frequency by means of a feedback loop. In the illustrated embodiment, the bender is configured as two separate crystals, thus using three electrical connections. The electrical connection on lead 16 is grounded to prevent cross-talk between the two plates 10 and 12. An AC voltage meter 60 is positioned to receive the output signal from lead 18 from the lower plate 12 of the bender. This meter provides data representing the amplitude and frequency of the output signal. This signal is also supplied to a controller 61 which is used to operate the mechanisms for adding additional ink and solvent to the mixing vessel 30 in the case of an ink jet printing application of FIG. 2. In other applications, other control circuitry may be employed to respond to the output signal 18 from the bender. The output 18 is also provided to an amplifier 62 which amplifies the output signal to a level required to drive the bender without saturating components. In order to drive the bender at is natural resonant frequency (for a given temperature and application environment) the phase of the signal from the amplifier 62 must be shifted by approximately ninety degrees, as is well known in the electrical arts. This is accomplished by a phase shift circuit 64 which receives the output signal from the amplifier 62 and which, in turn, outputs a phase shifted signal as an input to the bender via lead 14, to plate 10. When the sensor is to be used with conductive fluids, such as continuous jet inks, the fluid being monitored must be grounded to prevent cross-talk between the input and output sides of the bender. Alternatively a ground shield may be placed around the bender as part of the sensor structure.

Thus, this feedback circuitry is used to operate the bender by maintaining it at its natural resonant frequency. Changes in the amplitude of the voltage obtained on output lead 18 will then vary as a function of changes in the fluid being sensed as will now be described. Due to configuration and electronic variables, however, the phase shift may need to be optimized at slightly more or less than ninety degrees, but this can be easily determined for any given application.

Figure 4:
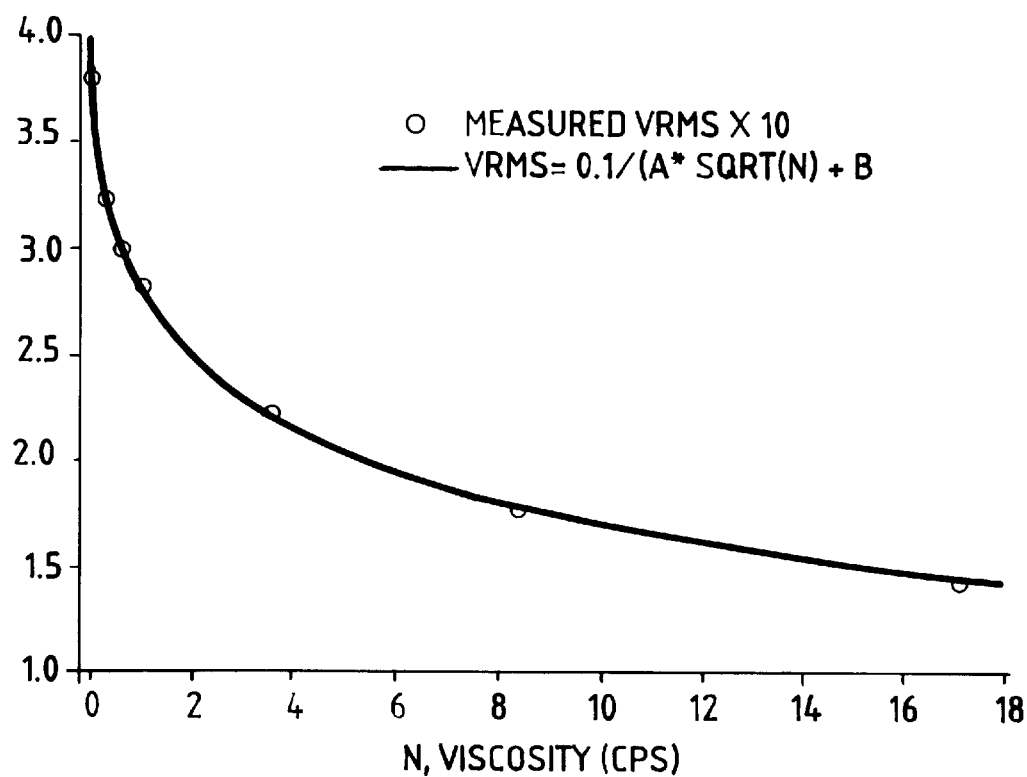
FIG. 4 is a data plot illustrating the manner in which the data obtained is utilized to determine viscosity and liquid level.

Referring to FIG. 4, the manner in which the output voltage on lead 18 is utilized to determine viscosity and fluid levels will be explained. Viscosity is measured by measuring the effects of viscous damping on the vibration of the vibrating structure. In the present invention, the vibrating structure is the bonded plates 10 and 12. The output signal on lead 18 is proportional to the amplitude of vibration of the bender. This output signal can be correlated to viscosity as illustrated in FIG. 4. As indicated, the voltage is an inverse function of viscosity. Specifically:

$$V_{rms} = 0.1/(A*\text{sqrt}(n)+B)$$

where:

A and B are empirically determined constants;

$V_{rms}$ is the root mean square voltage and n is viscosity.

As viscosity increases, the output voltage decreases and vice versa. Very low viscosity values indicate that the sensor is no longer in a liquid. Thus, a liquid level detection function is also performed.

The values A and B are unique to the sensor used to collect the data. The vibrating structure is driven at its fundamental resonant frequency by placing a voltage signal of proper amplitude and frequency on the bender. The frequency is dependent upon the environment in which the sensor operates and, for example, temperature can have a material affect on the frequency. By fitting an equation correlating output voltage and viscosity, a convenient method is provided for calibrating the sensor. Ideally, the manufacturing process for the benders produces sensors with minimal sample variation and it is not expected that individual calibration will be required. Because the performance of the benders is highly temperature dependent, temperature compensation algorithms must be used and are easily developed by those skilled in this art by fitting an equation to temperature calibration data. An alternative is to use a calibration or reference sensor maintained at the same temperature. Thus, for example, in this case of FIG. 2, the output voltage from the bender 50 used to monitor the level and viscosity of the ink in the mixing vessel 30 may be compared with the output of the bender 56 in vessel 34 which contains only fresh ink. In this manner, the temperature effect on the sensors may be nullified, provided that the two vessels are maintained at the same temperature.

As indicated previously, the sensor of the present invention detects both the viscosity of a fluid in a vessel and liquid level in a vessel since the viscosity of a gas is significantly less than that of most fluids of interest. It is for this reason that the benders 52 and 54 may be provided in the mixing vessel 30. Thus, when the ink level in the vessel is at or above the level of a bender, the viscosity reading determined from the curve of FIG. 4, will indicate the presence of a liquid. On the other hand, when the bender is no longer immersed in a liquid, but is operating in air, its viscosity value will drop significantly, almost to zero, indicating that the liquid is below the level of the bender. Thus, benders 50, 52 and 54 in tank 30 provide an indication of the liquid level in the vessel 30 by signalling a major viscosity change as liquid drops below their positions.

Where the benders are intended for use with control systems as, for example, in the embodiment illustrated in FIG. 2, the voltage output on lead 18 of FIG. 3, is typically converted to an analog DC signal and then to a digital signal and provided to a micro-processor based controller 61 which, for example, will compare the information against a selected value or reference measurement and, when called for, add fresh ink or solvent to the mixing vessel 30. The reference measurement may be provided from bender 56. In addition, it can be programmed to determine alarm conditions such as a lack of ink in the mixing vessel 30 as would be the case for example, if bender 50 were to signal a very low viscosity. Thus, if fresh ink reservoir 34 was empty, eventually the mixing vessel 30 would empty and require that printing cease in order to prevent unintended operation of the system.

In summary, when the voltage output on lead 18 is less than a certain threshold (on the order of 80% of the voltage for air) this is an indication that liquid is present. When the voltage amplitude is above that threshold, it means that the bender is no longer immersed in liquid and therefore the fluid level in the vessel has fallen below the position of the bender. In the event that the voltage indicates that liquid is present at the bender, than the voltage magnitude may be used to determine the viscosity of the liquid. This information can be used by a controller to modify that viscosity by the addition of solvent, fresh ink or other components as desired.

In addition to liquid level and viscosity, the present invention can be used to make density measurements. Density can be measured by measuring the effects of mass loading on the vibration of the bender structure. To do so, it is necessary to monitor the frequency of the output voltage signal rather than the magnitude. This signal has a frequency equal to the fundamental resonant frequency of the vibrating structure which can be correlated to density. The main effect of mass loading is to reduce the fundamental resonant frequency. The density measurement capability of the present invention can be used to distinguish liquids from gas because the density of gas is, of course, significantly less than that of a liquid. In order to calibrate density with the frequency of the output voltage, a graph similar to FIG. 4 is produced from data points taken for a given system. The graph would have density on its horizontal axis and frequency on its vertical axis. For a constant viscosity, the density of a fluid being monitored by the bender is determined by the equation:

$$D = A f[(1/Q)-B]^{-2}$$

where A and B are constants Q is the resonant Q value and f is frequency

As indicated previously, other piezoelectric ceramic devices can be used according to this invention, including another Morgan Matroc bender sold under the trade name Unimorph® which is a thin piezoelectric bender with two surfaces of dissimilar composition. Unlike the Bimorph® bender which is a two-port device, the Unimorph is a one-port device. A method for measuring the effects of viscous damping and mass loading that does not require two ports must be used to employ a one-port bender as a fluid properties sensor. One such method is that of measuring the changes in motional impedance or resistance as described for example, in "Acoustic Wave Micro Sensors" *Analy. Chem.* 1993 #65, pp. 987–996. Motional resistance, R, is the change in circuit resistance due to viscous damping. It can be measured using a network analyzer or equivalent circuit. Viscosity, v, is related to motional resistance as follows:

$$v = K f R^2 / r$$

where:

K is a constant, R is the motional resistance, r is density, and f is the resonant frequency of the bender.

Figure 5:
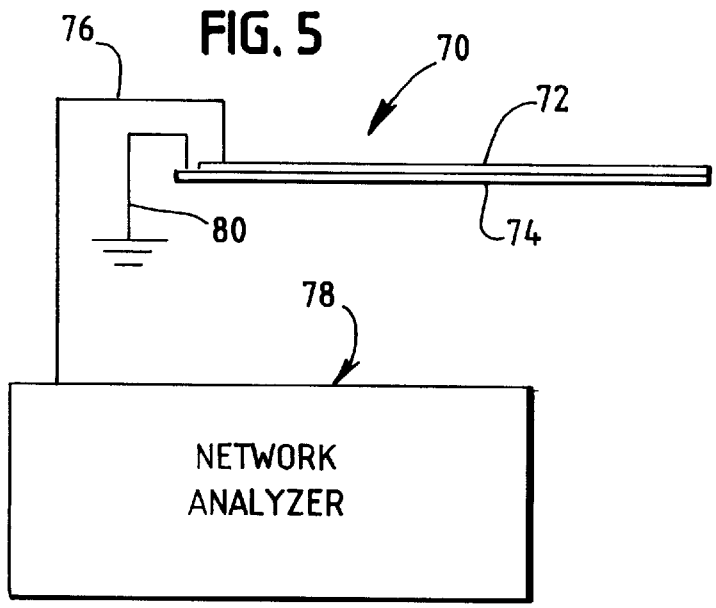
FIG. 5 is a block diagram similar to FIG. 3 for a single port bender.

Referring to FIG. 5, there is shown a block diagram of a circuit for use with a one-port bender in order to determine viscosity by measuring motional resistance R. The one-port or Unimorph device 70 has dissimilar surfaces 72 and 74. One surface is electrically connected via lead 76 to a network analyzer or similar circuit indicated at 78. For example, a Hewlett Packard HP 8751A Network Analyzer is suitable. The other surface is grounded via lead 80. In operation, a voltage from the analyzer is applied to the bender via lead 76. The analyzer, as is well known, measures the resistance of the circuit, which in this case is the motional resistance R. The viscosity is then computed using the formula.

While preferred embodiments of the present invention have been illustrated and described, it will be understood by those of ordinary skill in the art that changes and modifications can be made without departing from the invention in its broader aspects. Various features of the present invention are set forth in the following claims.

What is claimed is:

1. A method of monitoring liquid viscosity to maintain the level of a liquid contained in a vessel comprising the steps of:
   (a) locating at least the vibrating portion of a piezoelectric bender in said vessel containing said liquid;
   (b) applying a stimulation voltage to said bender at an amplitude and frequency to cause the bender to resonate;
   (c) varying said stimulation voltage frequency as a function of said output voltage frequency to maintain said bender at resonance;
   (d) monitoring an output voltage from said bender, the amplitude of said output voltage varying as an inverse function of the liquid viscosity, whereby an increase in liquid viscosity produces a decrease in output voltage amplitude and vice-versa;
   (e) detecting when the output voltage amplitude signals a change in viscosity indicating that the bender is no longer in contact with said liquid; and
   (f) automatically replenishing the liquid in said vessel when the liquid is no longer in contact with said bender.

2. The method of claim 1 wherein step (b) includes the sub-step of employing a feedback circuit to amplify and phase shift said output voltage to produce said stimulation voltage applied to said bender.

3. Apparatus for monitoring liquid viscosity to maintain the level of a liquid contained in a vessel comprising:
   (a) a piezoelectric bender having an element which vibrates upon application of a stimulation voltage thereto and which is positioned to contact said liquid;
   (b) means for applying a stimulation voltage to said bender at an amplitude and frequency to cause said bender element to resonate and to produce an output voltage,
   (c) means for varying said stimulation voltage frequency as a function of said output voltage frequency to maintain said bender at resonance;
   (d) means for monitoring an output voltage from said bender, the amplitude of said output voltage varying as an inverse function of the liquid viscosity, whereby an increase in liquid viscosity produces a decrease in output voltage amplitude and vice-versa;
   (e) means for detecting when the output voltage amplitude signals a change viscosity indicating that the bender is no longer in contact with said liquid; and
   (f) means for automatically replenishing said vessel when said output voltage indicates that said bender is no longer in contact with said liquid.

4. Apparatus according to claim 3 wherein said means for applying a stimulation voltage comprises a feedback circuit to amplify and phase shift said output voltage to produce said stimulation voltage applied to said bender.

5. Apparatus for monitoring and maintaining the viscosity of a liquid comprising:
   (a) a piezoelectric bender having an element which vibrates upon application of a stimulation voltage thereto and which is positioned to contact said liquid;
   (b) means for applying a stimulation voltage to said bender at an amplitude and frequency to cause said bender element to resonate and to produce an output voltage, the amplitude of which varies as an inverse function of liquid viscosity whereby an increase in liquid viscosity produces a decrease in output voltage amplitude and vice-versa;
   (c) said means for applying including means for varying said stimulation voltage frequency responsive to said output voltage frequency to maintain said bender at its resonant frequency in said liquid; and
   (d) means for automatically altering the liquid viscosity responsive to the amplitude of said output voltage.

6. A method for monitoring and maintaining the viscosity of a liquid comprising:
   (a) locating the vibrating portion of a piezoelectric bender in contact with said liquid;
   (b) applying a stimulation voltage to said bender at an amplitude and frequency to cause said bender to resonate and to produce an output voltage, the amplitude of which varies as an inverse function of liquid viscosity, whereby an increase in liquid viscosity produces a decrease in output voltage amplitude and vice-versa;
   (c) varying said stimulation voltage frequency as a function of said output voltage frequency to maintain said bender at resonance; and
   (d) automatically altering the liquid viscosity responsive to the amplitude of said output voltage.

7. A resonator sensor for monitoring changes in the properties of a liquid such as density and viscosity comprising:
   (a) a one-port bender;
   (b) means for causing said bender to vibrate in said liquid at its resonant frequency; and
   (c) monitoring the changes in the electrical characteristics of said bender due to changes in the motional resistance of said liquid to determine changes in said liquid properties.

8. A liquid sensing apparatus comprising:
   (a) a piezoelectric bender for immersion in the liquid;
   (b) a first circuit (62,64) for supplying an input voltage to said bender at a frequency to cause it to resonate; and (c) a second circuit (60) for monitoring an output voltage produced by said bender in response to said input voltage thereby to sense said liquid;

(d) said first circuit(62)receiving said output voltage and following any change in the resonant frequency of said bender thereby to maintain the bender at resonance, said first circuit maintaining said input voltage amplitude substantially constant, independent of any change in the amplitude of said output voltage.

9. Apparatus according to claim 8 wherein an amplitude of said output voltage is used to monitor the viscosity of said liquid.

10. Apparatus according to claim 9 wherein said viscosity is used to determine whether a surface of said liquid is above or below the level of said piezoelectric bender.

11. Apparatus according to claim 10 wherein said liquid is in a container, and wherein more liquid is added to said container if said liquid surface is below the level of said piezoelectric bender.

12. Apparatus according to claim 9 wherein said viscosity is altered if said viscosity is outside a predetermined range.

13. Apparatus according to claim 8, wherein a frequency of said output voltage is used to monitor the density of said liquid.

14. Apparatus according to claim 13 wherein said density is used to determine whether a surface of said liquid is above or below the level of said piezoelectric bender.

15. Apparatus according to claim 8 wherein said means for maintaining said input voltage at a predetermined level comprises an automatic gain control (AGC) amplifier.

16. Apparatus according to claim 8 wherein said first circuit for supplying an input voltage further comprises a phase shift circuit for shifting the phase of said output voltage by substantially 90°.

17. Apparatus according to claim 8 wherein said piezoelectric bender is a two-port device, and said second circuit for monitoring monitors at least one of the amplitude and frequency of said output voltage.

18. Apparatus according to claim 8 wherein said piezoelectric bender is a one-port device, and said second circuit for monitoring monitors said output voltage (76) to monitor the motional resistance of the liquid being sensed.

19. A liquid sensing apparatus comprising:

(a) a piezoelectric bender for immersion in the liquid;

(b) a first circuit (62,64) for supplying an input voltage to said bender at a frequency to cause it to resonate; and (c) a second circuit (60) for monitoring an output voltage produced by said bender in response to said input voltage thereby to sense said liquid;

(d) said first circuit (62) receiving said output voltage and following any change in the resonant frequency of said bender thereby to maintain the bender at resonance, said first circuit including amplifying means for maintaining said input voltage below a predetermined level.

\* \* \* \* \*